United States Patent [19]

Astrinsky

[11] Patent Number: 4,892,102

[45] Date of Patent: Jan. 9, 1990

[54] CARDIAC PACING AND/OR SENSING LEAD AND METHOD OF USE

[76] Inventor: Eliezer A. Astrinsky, 2600-1-n Netherlands Ave., Riverdale, N.Y. 10463

[21] Appl. No.: 912,236

[22] Filed: Sep. 26, 1986

Related U.S. Application Data

[63] Continuation of Ser. No. 858,567, Apr. 24, 1986, abandoned, which is a continuation of Ser. No. 647,975, Sep. 6, 1984, abandoned, which is a continuation-in-part of Ser. No. 600,511, Apr. 16, 1984, abandoned.

[51] Int. Cl.$^4$ .............................................. A61B 5/02
[52] U.S. Cl. .............................. 128/642; 128/419 PG
[58] Field of Search ............. 128/419 P, 419 PG, 659, 128/642, 783, 784, 785, 786

[56] References Cited

U.S. PATENT DOCUMENTS

| | | | |
|---|---|---|---|
| 3,405,715 | 10/1968 | Hagfors | 128/784 |
| 3,825,015 | 7/1974 | Berkovits | 128/419 P |
| 3,857,398 | 12/1974 | Rubin | 128/419 P |
| 3,902,501 | 9/1975 | Citron et al. | 128/419 P |
| 4,125,116 | 11/1978 | Fischell | 128/419 P |
| 4,156,429 | 5/1979 | Amundson | 128/419 P |
| 4,280,514 | 7/1981 | MacGregor | 128/419 P |
| 4,281,668 | 8/1981 | Richter et al. | 128/784 |
| 4,365,639 | 12/1982 | Goldreyer | 128/786 |
| 4,402,328 | 9/1983 | Doring | 128/419 P |
| 4,458,695 | 7/1984 | Peers-Trevarton | 128/419 P |
| 4,493,329 | 1/1985 | Crawford et al. | 128/419 P |
| 4,579,119 | 4/1986 | Callaghan | 128/419 PG |

OTHER PUBLICATIONS

Foster "Electric Field Control Electrode for Stimulation of Peripheral Nerve" *conference: IEEE* 1979 *Frontiers of Engineering in Health Care* Denver Co, USA, pp. 213-214.

*Primary Examiner*—William E. Kamm
*Attorney, Agent, or Firm*—Hedman, Gibson, Costigan & Hoare

[57] ABSTRACT

A cardiac sensing and pacing lead primarily for transvenous insertion in the heart and connection to a pacemaker or other measuring or stimulating device. The lead includes a triple electrode configuration wherein three electrodes located axially along the lead are connected such that the two outer electrodes are electrically connected together and to a suitable input port, and the middle electrode is connected to the same input port forming a shielded bipolar sensing element which when inserted in the heart permits strong near field sensing and excellent far field rejection of electrical signals. Epicardial and myocardial lead versions of the above endocardial lead are also described.

14 Claims, 6 Drawing Sheets

CARDIAC PACING AND/OR SENSING LEAD AND METHOD OF USE

CROSS-REFERENCE TO RELATED APPLICATIONS

This application is a continuation application of U.S. Application Ser. No. 858,567 filed Apr. 24, 1986, now abandoned, which is a continuation of U.S. Application Ser. No. 647,975 filed Sept. 6, 1984, now abandoned, which is a continuation-in-part of U.S. Application Ser. No. 600,511 filed Apr. 16, 1984, now abandoned.

FIELD OF THE INVENTION

This invention relates to a sensing and pacing lead used with pacemakers or other cardiac measuring or stimulating devices. More particularly, the lead includes a shielded bipolar sensing element comprising a triple electrode configuration which permits strong near field sensing while rejecting far field signals and noise.

DESCRIPTION OF THE PRIOR ART

Heart pacemakers utilize leads that are connected to the heart through a vein. An electrode on the tip of the lead is placed in the ventricle for ventricular pacing. There are medical advantages for many patients to have the ventricular pacing synchronized with the P-wave signal emanating from the atrium. Thus, an atrial synchronous pacemaker was developed to permit this atrio-ventricular synchronization. A separate lead placed in the atrium is required. The additional atrial lead senses the P-wave from the atrium while the ventricular lead is used to correspondingly stimulate or pace the ventricle.

The two types of leads used in the atrium have been unipolar and bipolar. The unipolar lead has not proven satisfactory in synchronous pacing since there is much difficulty in determining the difference between the endocardial P-wave and R-wave as measured in the atrium. Thus, the R-wave may be sensed as a P-wave thereby pacing the ventricle ineffectively as the ventricle cannot respond to stimulation during the refractory period which follows immediately after depolarization. Bipolar leads have proved better for discriminating between P and R-waves, but with the standard two electrode configuration being used a substantial R-wave is still detected which may cause problems distinguishing between atrial and ventricular events.

Thereafter, it was determined that a single lead having an electrode at the tip, for ventricular pacing and electrodes a certain distance away from the tip which would lie in the atrium for atrial sensing would be advantageous.

In U.S. Pat. No. 4,365,639, issued to Goldreyer, a single lead having an orthogonal electrode configuration is disclosed. Two pairs of opposed electrodes are mounted circumferentially around the catheter and are connected to produce two bipolar signals sensed from the atrium. A high amplitude P-wave signal is sensed by the Goldreyer configuration with minimum QRS complex amplitudes. A major deficiency of the Goldreyer lead is the difficulty in manufacturing the lead. Furthermore, the electrodes have a small area on the catheter on which to be attached thereby making it a fragile apparatus. In addition, the orthogonal configuration is position sensitive to a point where patient movement may decrease the discriminatory advantages of the system.

An SRT lead, disclosed in CPI brochure No. 4-534-481, has been attempted in a modification of the Goldreyer configuration. A pair of electrodes are angularly spaced by 120° instead of the 180° required by Goldreyer. However, the circumferential location of the pair of electrodes may still present manufacturing difficulties since non-standard electrodes are being used.

U.S. Pat. No. 3,659,933 issued to Hagfors is directed to implantable electrodes for nerve stimulation. The electrodes are flexible flat pieces of metal that can be wrapped around a nerve trunk. A guarded electrode configuration is disclosed for providing improved current density. A pair of flat electrodes are connected to one lead and a central, wider flat electrode is connected to a second lead. The leads are encapsulated in a substance inert to body fluids and tissue. The Hagfors electrode apparatus is not designed for endocardial or epicardial use. Hagfors is solely directed to stimulation of nerve trunks dissected out and contained within the electrode insulating sheath. This configuration has also been modified for sensing from isolated nerve trunks.

A pill electrode having a quadrupole electrode configuration is disclosed by Arzbaecher in IEEE article 13.4.1, 1982. The quadrupole electrode, as shown in FIG. 2 of the above article has two positive poles and its two negative poles are combined into one at the center for convenience. The pill electrode is swallowed by the patient and remains in the esophagus immediately posterior to the left atrium. The pill electrode is a detection device used for identification of complex arrhythmia and other monitoring applications. The Arzbaecher electrode is not directed to tranvenous implantation into the heart for atrial and ventricular sensing and pacing.

SUBJECT OF THE INVENTION

Accordingly, it is an object of the subject invention to provide a cardiac lead having a shielded bipolar electrode configuration which provides good near field detection and far field rejection of electrical signals.

It is another object of the subject invention to provide a single endocardial lead that can provide both atrial sensing and ventricular pacing.

In accordance with the invention, there is provided an endocardial lead having a shielded bipolar sensing element comprising first, second and third electrodes located axially along the lead. The lead is inserted in the heart and connected to a pacemaker for atrial or ventricular sensing and pacing. In addition, the lead may be used in connection with measuring devices as a sensing lead.

The first and third electrodes are electrically connected together to form one pole connected to a first terminal. The second or central electrode is connected directly to a second terminal forming the second pole, thereby forming a bipolar element. The first and second terminals may be connected to any measuring or sensing device or to a pacemaker. This triple electrode configuration, unique to endocardial lead systems, provides shielding of the central electrode by the two outer electrodes. Thus, near field cardiac signals are focused and concentrated in the region between the first and third electrodes while far field signals are cancelled.

The triple electrode configuration permits the use of standard ring electrode fabrication technology while providing excellent stability and ease of manufacture.

In addition to the shielded bipolar electrode configuration, a fourth electrode can be provided at the tip of the lead to enable stimulation via the tip electrode and sensing via the shielded bipolar electrode configuration. The endocardial lead according to the invention is particularly adapted for sensing atrial signals while cancelling ventricular artifacts. When the lead is used with an atrial synchronous pacemaker, the lead is introduced transvenously into the heart so that the distal tip electrode is positioned in the apex of the right ventricle and the shielded bipolar sensing element is floating in and adjacent to the wall of the high right atrium. The pacemaker then senses atrial depolarization through the sensing element and can stimulate the ventricle through the tip electrode.

In another embodiment, the single endocardial lead may have two separate shielded bipolar sensing elements, one in the atrium and one in the ventricle for atrial and ventricular sensing together with a ventricular pacing electrode at the distal tip of the lead.

Other embodiments include the lead having the triple electrode configuration and stimulating electrode being used only in the atrium for atrial sensing and pacing. In this case, the sensing element of the subject invention may be utilized on a J lead for atrial sensing or together with a tip electrode for atrial sensing and pacing. Alternatively, the shielded bipolar sensing element and stimulating electrode may be used only in the ventricle for ventricular sensing and pacing.

An alternative to the use of a single electrode for atrial ventricular synchronized pacing is the use of a pair of separate leads as described above, the first for atrial sensing and the second for ventricular pacing. If dual chamber universal pacing is to be implemented (DDD mode) with both atrial and ventricular sensing and pacing, then a J lead with shielded sensing and unipolar pacing elements could be used in the atrium and a separate lead with shielded sensing and unipolar pacing elements could be used in the ventricle.

In addition, the triple electrode configuration may be used for cardiac pacing in either the ventricle or atrium. When used for pacing, there is reduced spread of stimulating current into adjacent tissues compared with unipolar or ordinary bipolar pacing electrodes. Unwanted stimulation of the phrenic nerve or the diaphragm should therefore be reduced.

Furthermore, there is provided an epicardial lead for attachment to the surface of the heart for sensing and or stimulating the heart. The epicardial lead includes a shielded or balanced differential electrode arrangement having three electrode elements mounted on an insulating means. In use, the electrodes are in contact with the heart. In one embodiment of the epicardial lead, the electrodes are arranged in a linear fashion with the outer two electrodes being electrically connected and connected to a first terminal and the third central electrode being connected to a second terminal.

A second embodiment of the epicardial lead includes the electrodes arranged symmetrically in a triangular configuration so that any pair of electrodes can be electrically connected together to the first terminal and the third electrode being connected to the second terminal.

Similarly, a myocardial lead is provided having the three electrodes penetrate the surface of the heart.

DETAILED DESCRIPTION OF THE PREFERRED EMBODIMENTS

Figure 1:
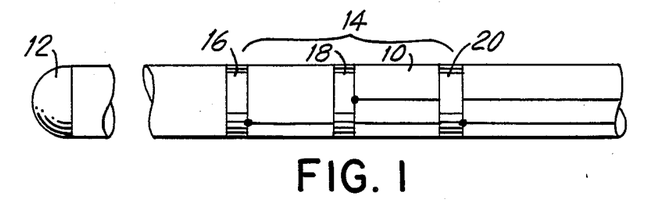
FIG. 1 is a plan view of the endocardial lead of the invention showing the electrode configuration positioned for atrial sensing and ventricular pacing.

Referring now to FIG. 1, there is shown a preferred embodiment of the lead 10 according to the subject invention. The lead 10 has a stimulating electrode 12 located at the tip of the lead 10. The stimulating electrode 12 is used for ventricular pacing when placed in the ventricle or atrial pacing when placed in the atrium. The stimulating electrode 12 is electrically connected to a pacemaker unit or other stimulating or measuring device (not shown). A three ring bipolar sensing element 14 is located on the lead 10 and comprises electrodes 16, 18 and 20 located axially along the lead 10. The electrodes 16, 18 and 20 are substantially equi-distant from each other. The center to center distance between the electrodes can be from one centimeter to as close as one millimeter. The preferred distance is a 3.5 mm center to center separation. The axial length of each ring electrode can be from 0.1 to 10 mm. The preferred length is 1.5 mm. The rings may be of different lengths but the preferred embodiment has equal rings. The central electrode 18 is electrically connected to a first terminal of the pacemaker unit or other measuring device. The outside electrodes 16 and 20 are electrically connected together and are also electrically connected to a second terminal of the pacemaker unit or measuring device. Hence, the three electrodes 16, 18 and 20, configured in this manner form the shielded bipolar sensing element 14. The outer two electrodes 16 and 20 being connected together provide shielding of the central electrode 18. Near field signals, originating from the section of the heart immediately adjacent to the sensing element 14, are detected while far field signals, originating from distant sections of the heart or elsewhere, are blocked or cancelled.

Furthermore, there may be applications such as where rejection of pacemaker pulses originating close to the sensing element 14 is essential where one of the outside electrodes 16 or 20 is at a greater distance from the central electrode 18 than the distance between the other outside electrode and the central electrode 18. In these applications, there will also be excellent blocking of far field signals and detection of near field signals by the shielded sensing element 14. In addition, a pair of resistors of substantially equal resistance may be placed in the line connecting electrodes 16 and 20. One of the resistors will be placed between the electrical connection point and electrode 16 and the other will be between the electrical connection point and the electrode 20.

Figure 5:
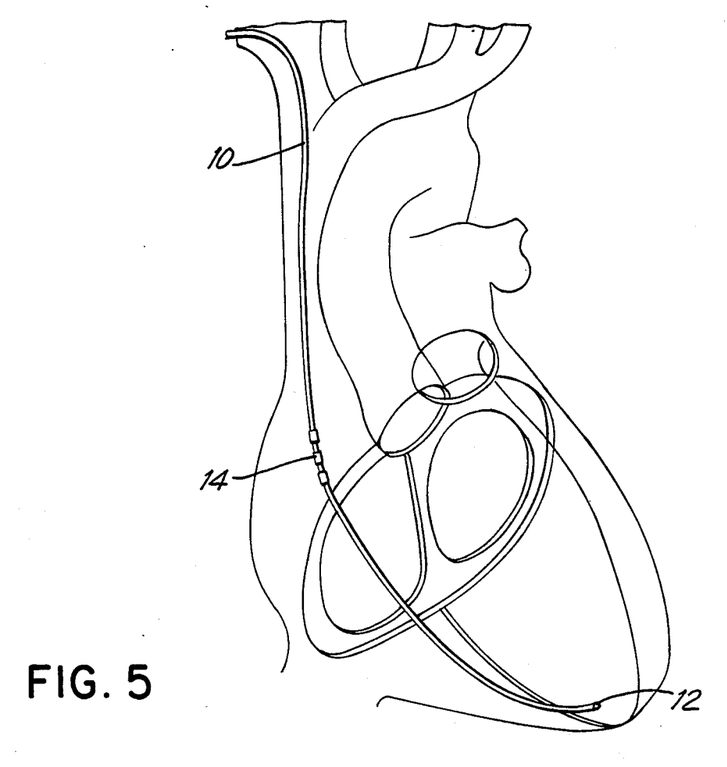
FIG. 5 is a plan view of the heart showing the placement of the lead of FIG. 1 of the invention.

In the embodiment of FIG. 1, the shielded bipolar sensing element 14 is used for atrial sensing and is located at a position on the lead 10 such that the element 14 lies in the atrium of the patient's heart. FIG. 5 shows the preferred embodiment after transvenous insertion in the heart wherein the stimulating electrode 12 is located in the right ventricle and the bipolar sensing element 14 is located in the right atrium. Thus, a strong atrial signal corresponding to a surface ECG's P-wave will be detected by sensing element 14. At the same time, ventricular depolarization, myopotentials and other electrical signals originating from distant sections of the heart or body will be rejected thereby permitting accurate interference-free atrial synchronous ventricular pacing.

The electrodes 12, 16, 18 and 20 can be made of materials suited for implantation such as platinum or platinum-iridium, carbon, or an alloy known by the trade name of Elgiloy commercially available from the Elgin Watch Co.

Figure 2:
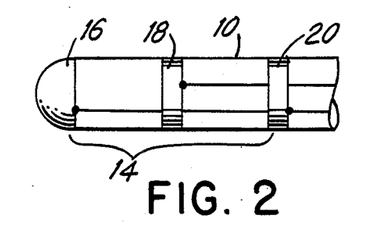
FIG. 2 is a plan view of the lead of FIG. 1 showing the electrode configuration positioned at the tip.

Sensing element 14 can be located anywhere along the lead 10 including the distal end. FIG. 2 shows the sensing element 14 wherein the outside electrode 16 is located at the distal end of the lead. The embodiment of FIG. 2 may be used for either ventricular or atrial sensing. The bipolar element 14 may also be used for pacing. The stimulating currents are focused in the region between electrodes 16 and 20 without significant spreading experienced with unipolar or the standard bipolar pacing electrode.

Figure 6:
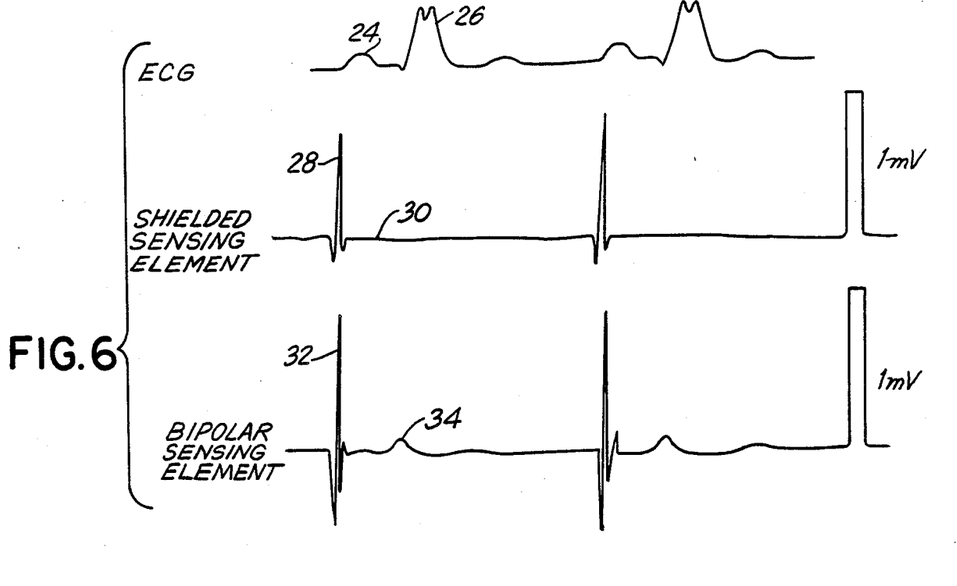
FIG. 6 is an illustration of the electrogram results obtained by the present invention compared to the prior art.

FIG. 6 is an illustration of the results obtained when the lead 10 is used for atrial sensing. The bipolar sensing element 14, by transvenous insertion is placed in the atrium. The upper tracing is an electrocardiogram showing the surface ECG's P-wave 24 and the QRS wave 26. The central tracing shows the endocardial P-wave 28 and the endocardial QRS wave 30 as sensed by the sensing element 14. As can be seen, the QRS wave is practically negligible, while the P-wave is a distinct easily detectable atrial signal. The lower tracing shows the results using a standard bipolar electrode placed in the atrium. The P-wave 32 is not as sharp a signal as with the subject invention and the far field QRS 34 is significantly larger. The central tracing illustrates the improved signal to noise ratio as compared with the lower tracing.

Figure 7:
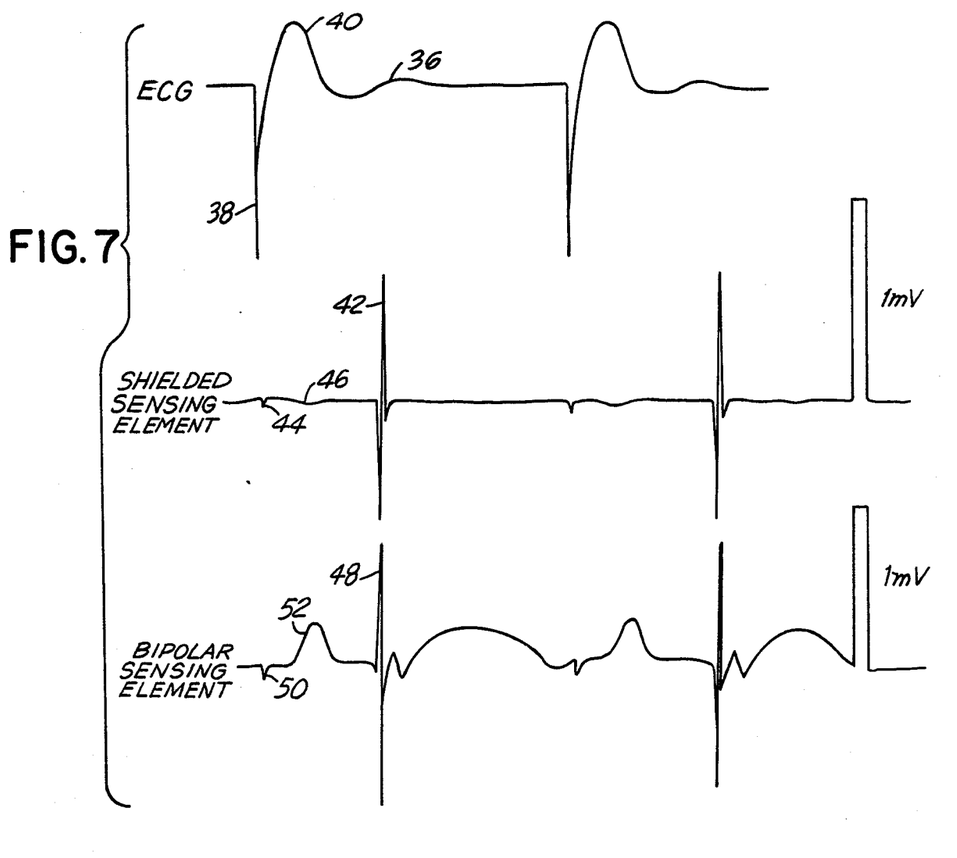
FIG. 7 is an illustration of the electrogram results obtained by the present invention compared to the prior art when the ventricle is being paced.

FIG. 7 is an illustration of the results obtained when the lead 10 is inserted in the atrium and a separate lead is used to pace the ventricle. The upper trace is the surface ECG showing the retrograde P-wave 36, ventricular pacer pulse 38 and the QRS 40. The middle trace shows the sharp endocardial P-wave 42 sensed by the sensing element 14, a near zero pacer artifact 44 and the minimal endocardial QRS 46. The sensing element 14 almost completely rejects the ventricular pacer pulse. The lower trace shows the results using a standard bipolar lead showing the P-wave 48, ventricular artifact in the atrium 50 and the endocardial QRS in the atrium 52. The shielded bipolar sensing element therefore provides superior rejection of far field ventricular pacing pulses and R-wave signals originating in the ventricle, while clearly detecting the P-wave in the atrium.

Figure 3:
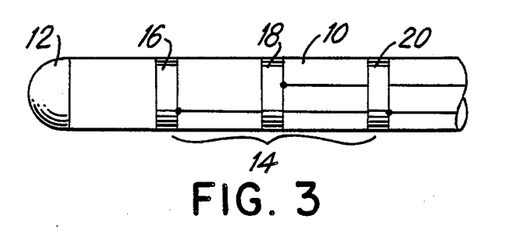
FIG. 3 is a plan view of the lead of FIG. 1 showing the electrode configuration positioned near the tip.
Figure 8:
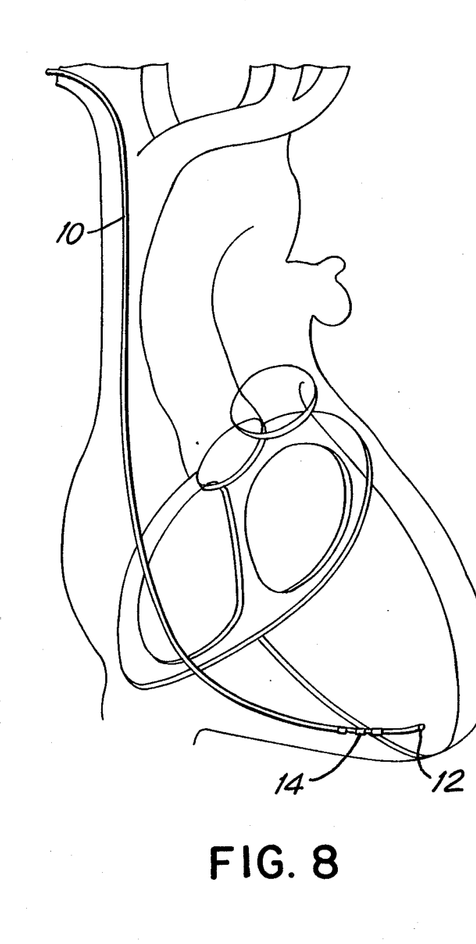
FIG. 8 is a plan view of the heart as in FIG. 5 showing the electrode configuration of FIG. 3 positioned for ventricular sensing and pacing.

In another embodiment shown in FIG. 3, the sensing element 14 is placed near the tip 12 which allows for both pacing and sensing in the same chamber. For example, by placing the lead 10 shown in FIG. 3 in the ventricle, as in FIG. 8, ventricular pacing and sensing can be performed. The embodiment of the invention as shown in FIG. 3 will permit sensing of ventricular depolarization immediately after pacing without the need for pacemaker rapid recharge circuits and long blanking periods. The same will occur when the lead 10 is placed in the atrium.

Figure 9:
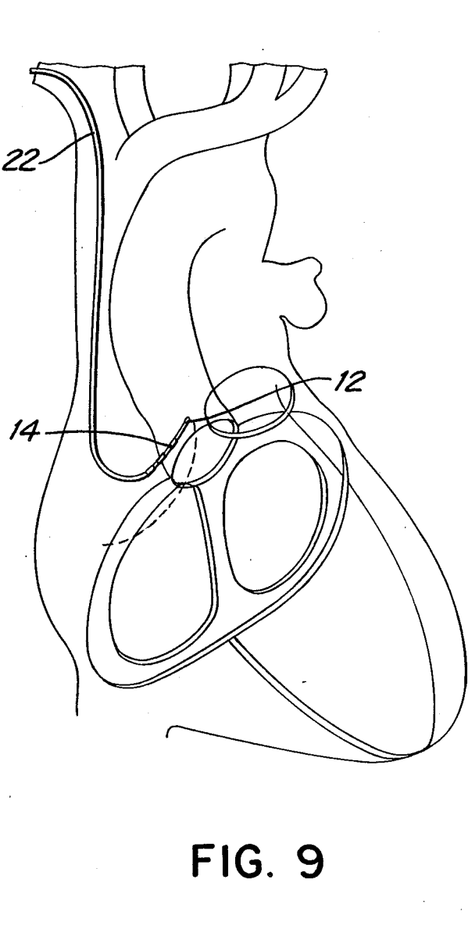
FIG. 9 is a view of the heart as in FIG. 5 showing a J lead version of FIG. 3.
Figure 10:
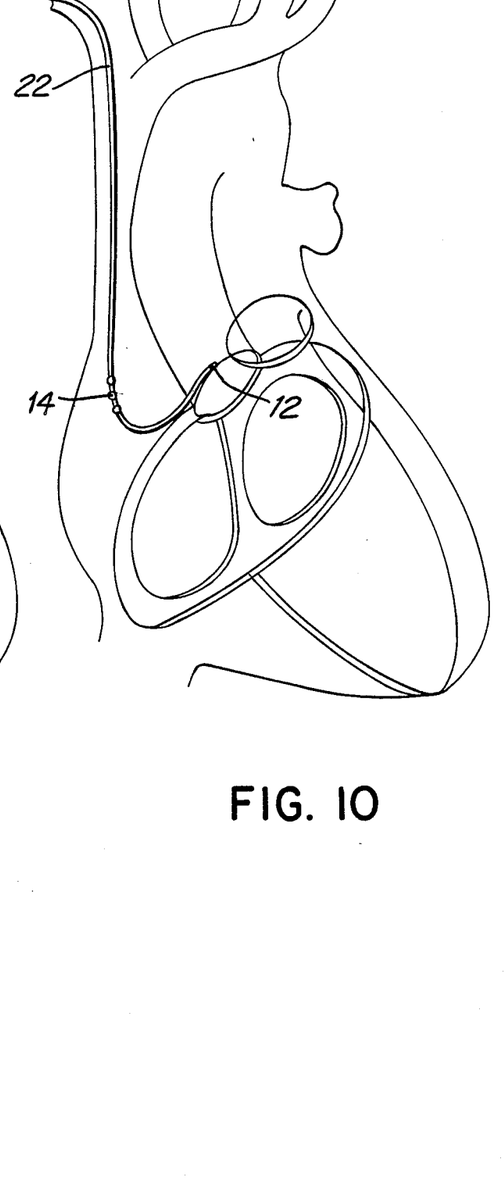
FIG. 10 is a plan view of the heart as in FIG. 5 showing a J version of FIG. 3 with the electrode configuration positioned for sensing from the high right atrium.

For atrial use, FIG. 9 shows the positioning of the sensing element 14 and the pacing element 12 when incorporated in a J lead 22 in the right atrial appendage. Further, as shown in FIG. 10, the J lead 22 may include the stimulating tip 12 located in the right atrial appendage and the sensing element 14 located on the J lead 22 such that the sensing element 14 is floating in the right atrium.

Figure 11:
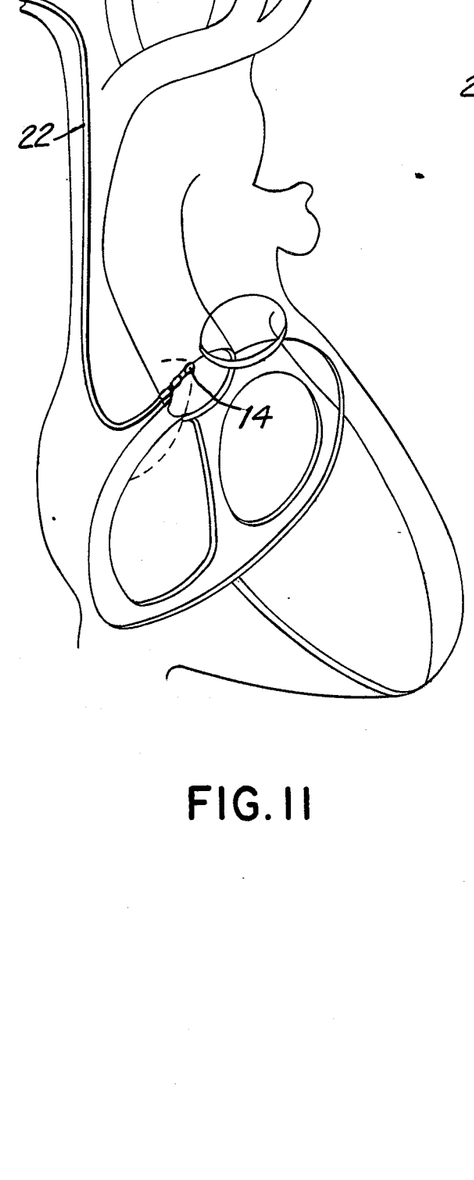
FIG. 11 is a plan view of the heart as in FIG. 5 showing a J lead version of FIG. 2 positioned for atrial sensing.

FIG. 11 shows the positioning of J lead 22, wherein one electrode of the sensing element 14 is located at the tip of the J lead 22 in the right atrial appendage.

Figure 4:
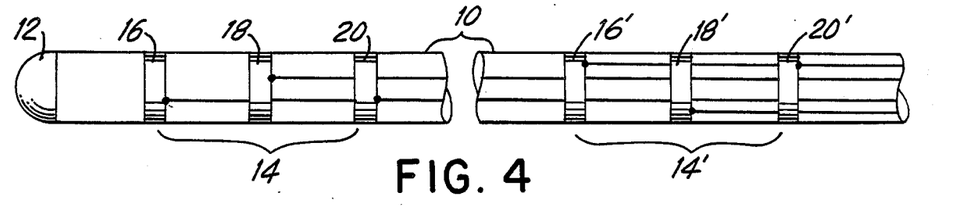
FIG. 4 is a plan view of the lead of FIG. 1 showing the electrode configuration positioned for ventricular sensing and pacing and atrial sensing.
Figure 12:
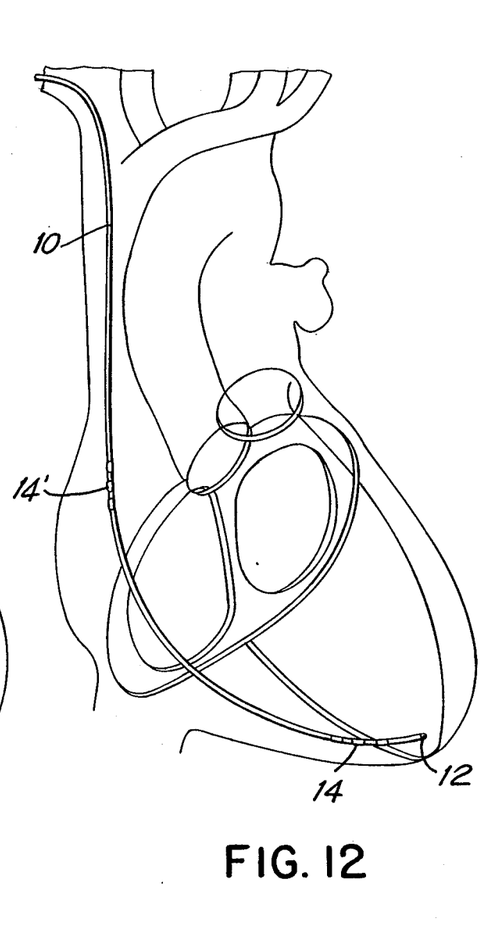
FIG. 12 is a plan view of the heart as in FIG. 5 showing the electrode configuration of FIG. 4 with the atrial sensing electrodes located in the atrium and the ventricular sensing and pacing electrodes in the ventricle.

The embodiment of FIG. 4 shows the lead 10 having the sensing element 14 positioned as in FIG. 3 with an additional sensing element 14' located away from the tip 12 as in FIG. 1. Thus, with the tip 12 and the sensing element 14 placed in the ventricle and the sensing element 14' placed in the atrium, there is provided a means for atrial sensing, ventricular sensing and ventricular pacing. This arrangement is shown in FIG. 12.

Figure 13:
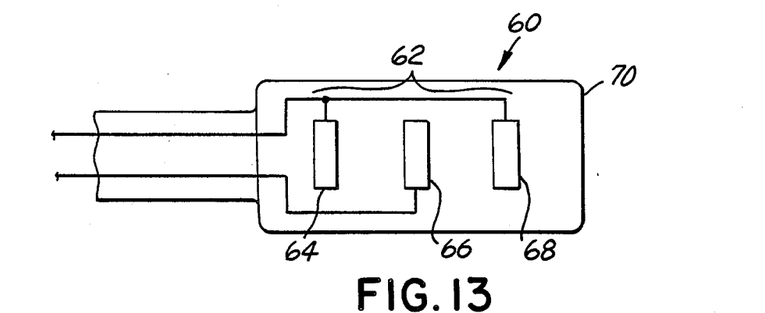
FIG. 13 is a plan view of the epicardial lead of the invention showing the electrodes aligned linearly.
Figure 14:
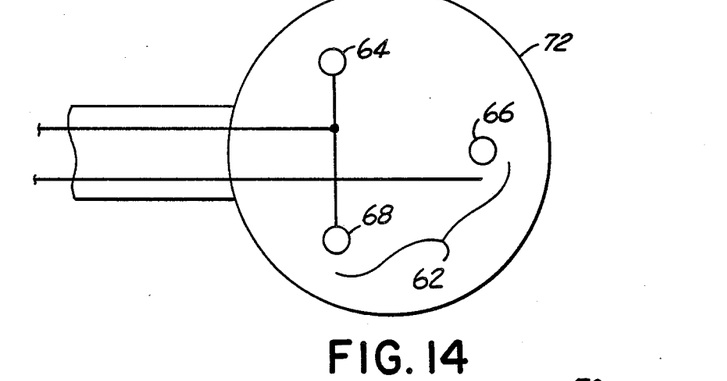
FIG. 14 is a plan view of another embodiment of the epicardial lead showing the electrodes arranged symmetrically.
Figure 15:
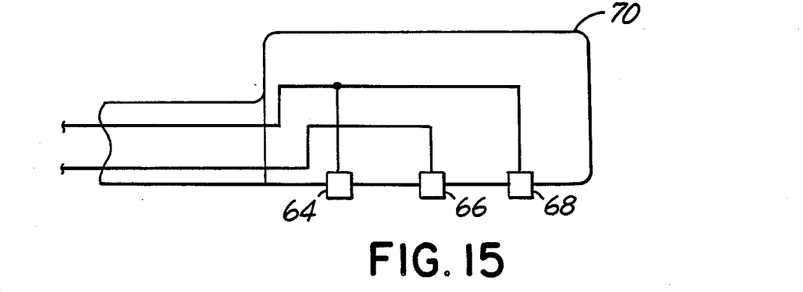
FIG. 15 is a side elevational view of lead of FIG. 13.

The epicardial lead of the invention is shown in FIGS. 13, 14 and 15. The epicardial lead 60 of FIG. 13 includes the shielded sensing element 62 with the electrodes 64, 66 and 68 aligned linearly and mounted on an insulating means 70. The electrodes 64 and 68 are electrically connected together and to a first terminal of the cardiac measuring or stimulating device (not shown). The electrode 66 is electrically connected to a second terminal of the cardiac device. The electrodes 64, 66 and 68 of the epicardial lead 60 protrude on end of the insulating means 70 in order to contact the surface of the heart as shown in FIG. 15.

The electrodes 64, 66 and 68 may be arranged symmetrically as in FIG. 14 on an epicardial lead having a circular insulating means 72. In FIG. 14, electrodes 64 and 68 are electrically connected together and connected to a first terminal of the cardiac measuring or stimulating device (not shown) being used and electrode 66 is electrically connected to a second terminal of the cardiac device. However, in this embodiment, any two electrodes may be electrically connected to form the bipolar element 62 and still have the properties of excellent detection of near field signals and cancelling of far field signals.

Figure 16:
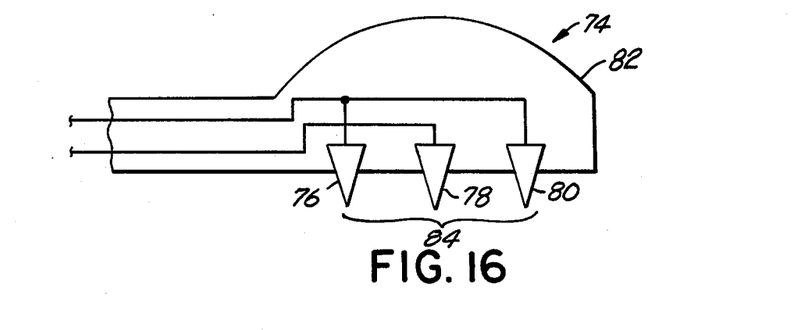
FIG. 16 is a side elevational view of the myocardial lead of the invention.

FIG. 16 shows a myocardial lead 74 wherein the electrodes 76, 78 and 80 protrude from one end of the insulating means 82 in a sharp point that pierces and grips the heart upon insertion. The shielded sensing element 84 is formed by electrically connecting electrodes 76 and 80 as discussed above.

The invention should not be limited to use with a pacemaker, as it can be used with any measuring or stimulating device. In addition to the uses stated above, the lead according to the invention may be used for recording from and accurate location of electrical pathways or electrically active tissues in the heart such as the Bundle of His, Atrio-Ventricular Node, a Kent Bundle, and a source of ectopic electrical activity. Once located, the invention may be used selectively for stimulating or for ablation of these tissues by passing current through the electrodes to these tissues.

While preferred embodiments of the subject invention have been described and illustrated, it is obvious that various changes and modifications can be made therein without departing from the spirit of the present invention which should be limited only by the scope of the appended claims.

What is claimed is:

1. A method for sensing electrical signals associated with muscular depolarization in a chamber of a heart without sensing electrical signals (a) associated with muscular depolarization in other chambers of the heart or (b) otherwise extraneous to the electrical signals being sensed and for pacing the heart, said method comprising the steps of:
   pacing a chamber of a heart;
   providing sensing circuitry;
   placing a sensor assembly mounted on an endocardial lead and including three spaced apart ring electrodes connected to the sensing circuitry, into a heart chamber;
   sensing, with the middle one of the three ring electrodes relative to the outer two electrodes placed in the one heart chamber, electrical signals associated with muscular depolarization in the one heart chamber,
   connecting the two outer electrodes together and to the sensing circuitry and connecting the middle ring electrode to the sensing circuitry;
   rejecting with the equi-potential state of the two outer ring electrodes in the heart in the area of the middle ring electrode, electrical signals (a) associated with muscular depolarization in other chambers of the heart or (b) otherwise extraneous to the electrical signals being sensed, thereby to prevent such other electrical signals from being sensed by the middle ring electrode.

2. The method of claim 1 including the step of providing a bipolar sensing system and wherein said step of rejecting is further accomplished by connecting the middle ring electrode to a first terminal of the bipolar sensing system and connecting said two outer ring electrodes to a second terminal of the bipolar sensing system.

3. The method of claim 1 wherein said step of sensing includes placing said endocardial lead in the atrium of the heart and placing said sensor assembly adjacent to a wall of the atrium to sense atrial depolarization.

4. The method of claim 1 wherein said pacing step includes pacing a second chamber of the heart in response to electrical signals sensed in the one chamber of the heart.

5. The method of claim 4 wherein said step of pacing is accomplished by providing a pacing electrode on a distal end portion of the endocardial lead so as to form an endocardial pacing lead and positioning the pacing electrode in a ventricle of the heart while at the same time positioning the sensor assembly in an atrium of the heart.

6. The method of claim 5 wherein said endocardial lead has a distal end and said step of pacing is further accomplished by placing the pacing electrode at the distal end of the endocardial lead, and placing the distal end at the apex of the ventricle.

7. Apparatus for sensing electrical signals associated with muscular depolarization in a chamber of a heart without sensing electrical signals (a) associated with muscular depolarization in other chambers of the heart or (b) otherwise extraneous to the electrical signals being sensed and for pacing the heart, said apparatus comprising:
   sensing/pacing circuitry;
   an endocardial lead;
   a pacing electrode on said endocardial lead connected to said sensing/pacing circuitry;
   a sensor assembly including three spaced apart ring electrodes coupled to said sensing/pacing circuitry and mounted on said endocardial lead for placement in one chamber of a heart for sensing with the middle ring electrode, electrical signals in the one chamber of the heart, said electrical signals being associated with muscular depolarization in the one chamber, and
   rejecting means including said two outer ring electrodes connected together and to said sensing/pacing circuitry for rejecting, in the heart, electrical signals (a) associated with muscular depolarization in other chambers of the heart or (b) otherwise extraneous to the electrical signals being sensed, thereby to prevent such other electrical signals from being sensed by said middle ring electrode.

8. The apparatus of claim 7 wherein said sensing/pacing circuitry includes a bipolar sensing system and said rejecting means includes a connection of said middle ring electrode to a first terminal of said bipolar sensing system and a connection of said two outer ring electrodes to a second terminal of said bipolar sensing system.

9. The apparatus of claim 7 wherein said endocardial lead has a distal end and wherein said sensing middle ring electrode is mounted on said lead body at a predetermined location from said distal end for placement of said sensor assembly adjacent to a wall of an atrium for sensing atrial depolarization when said endocardial lead is placed in the heart.

10. The apparatus of claim 7 wherein said pacing electrode is positioned on said endocardial lead at a location for pacing a second chamber of the heart in response to electrical signals sensed in the one chamber of the heart.

11. The apparatus of claim 10 wherein said endocardial lead has a distal end portion and said pacing electrode is mounted on said distal end portion of said endocardial lead so as to form an endocardial pacing lead, said sensing middle ring electrode being located at a predetermined distance from said pacing electrode whereby, when said lead is placed in a heart, said pacing electrode is located in the ventricle and said sensing electrode is located in the atrium of the heart.

12. The apparatus of claim 11 wherein said endocardial lead has a distal end and said pacing electrode is mounted at said distal end of said endocardial lead, whereby said pacing electrode can be placed at the apex of the ventricle.

13. A method for sensing electrical signals associated with muscular depolarization in a chamber of a heart without sensing electrical signals (a) associated with muscular depolarization in other chambers of the heart or (b) otherwise extraneous to the electrical signal being sensed, said method comprising the steps of:

providing sensing circuitry;

placing a sensor assembly, mounted on an endocardial lead and including three spaced apart ring electrodes connected to the sensing circuitry, into a heart chamber;

sensing, with the middle one of the three ring electrodes relative to the outer two electrodes placed in the one heart chamber, electrical signals associated with muscular depolarization in the one heart chamber, connecting the two outer electrodes together and to the sensing circuitry connecting the middle ring electrode to the sensing circuitry;

rejecting with the equi-potential state of the two outer ring electrodes in the heart in the area of the middle ring electrode, electrical signals (a) associated with muscular depolarization in other chambers of the heart or (b) otherwise extraneous to the electrical signals being sensed, thereby to prevent such other electrical signals from being sensed by the middle ring electrode.

14. Apparatus for sensing electrical signals associated with muscular depolarization in a chamber of a heart without sensing electrical signals (a) associated with muscular depolarization in other chambers of the heart or (b) otherwise extraneous to the electrical signals being sensed and for pacing the heart, said apparatus comprising:

sensing circuitry;

an endocardial lead;

a sensor assembly including three spaced apart ring electrodes coupled to said sensing circuitry and mounted on said endocardial lead for placement in one chamber of a heart for sensing with the middle ring electrode, electrical signals in the one chamber of the heart, said electrical signals being associated with muscular depolarization in the one chamber, and rejecting means including the two outer ring electrodes connected together and to said sensing circuitry for rejecting, in the heart, electrical signals (a) associated with muscular depolarization in other chambers of the heart or (b) otherwise extraneous to the electrical signals being sensed, thereby to prevent such other electrical signals from being sensed by said middle ring electrode.

* * * * *